(12) United States Patent
Kornbluth et al.

(10) Patent No.: US 12,203,827 B2
(45) Date of Patent: Jan. 21, 2025

(54) SYSTEM FOR SENSING WATER QUALITY OR LEAKS USING APPLIANCE DATA AND MACHINE LEARNING

(71) Applicant: Robert Bosch GmbH, Stuttgart (DE)

(72) Inventors: Mordechai Kornbluth, Brighton, MA (US); Soo Kim, Arlington, MA (US); Jonathan Mailoa, Cambridge, MA (US); Charles Tuffile, Swansea, MA (US)

(73) Assignee: Robert Bosch GmbH (DE)

( * ) Notice: Subject to any disclaimer, the term of this patent is extended or adjusted under 35 U.S.C. 154(b) by 189 days.

(21) Appl. No.: 17/406,642

(22) Filed: Aug. 19, 2021

(65) Prior Publication Data

US 2023/0060059 A1    Feb. 23, 2023

(51) Int. Cl.
*G01M 3/26* (2006.01)
*G01N 33/18* (2006.01)

(52) U.S. Cl.
CPC .............. *G01M 3/26* (2013.01); *G01N 33/18* (2013.01)

(58) Field of Classification Search
CPC ............ E03B 7/003; E03B 7/07; G01M 3/00; G01M 3/26; G01N 33/18; G08B 21/20; H04L 12/2816; Y10T 137/0379
See application file for complete search history.

(56) References Cited

U.S. PATENT DOCUMENTS

| | | | |
|---|---|---|---|
| 8,456,312 B2 | 6/2013 | Wofford | |
| 10,526,771 B1* | 1/2020 | Devereaux | E03B 7/003 |
| 11,061,416 B2* | 7/2021 | Ravid | A61B 5/7282 |
| 11,087,497 B2* | 8/2021 | Huertas Carrillo | G06N 20/00 |
| 2016/0179105 A1 | 6/2016 | Cregg | |
| 2019/0025150 A1* | 1/2019 | Picardi | G05B 23/0218 |
| 2020/0393324 A1* | 12/2020 | Rudd | G08B 19/00 |
| 2021/0301985 A1* | 9/2021 | Brown | G05B 23/0221 |
| 2021/0355659 A1* | 11/2021 | Kim | G01M 3/243 |
| 2022/0049478 A1* | 2/2022 | Mason | G01F 25/10 |

FOREIGN PATENT DOCUMENTS

CN        211402225 U       9/2020

* cited by examiner

*Primary Examiner* — Huy Q Phan
*Assistant Examiner* — Martin Walter Braunlich
(74) *Attorney, Agent, or Firm* — Dickinson Wright PLLC

(57) ABSTRACT

Systems and methods for monitoring the quality of water or leaks within a household plumbing system via machine learning are provided. Appliances can be connected to a plumbing system, wherein each appliance includes one or more sensors configured to output sensor data regarding a property of the water being utilized by that appliance. A processor is programmed to receive the sensor data and establish boundaries of normal operation. Then, when additional sensor data is received, the processor uses machine learning to classify that sensor data as being either within normal operation, or outside the bounds of normal operation. If the sensor data indicates the water property is outside the bounds, an output signal can be generated to inform the user.

16 Claims, 5 Drawing Sheets

SYSTEM FOR SENSING WATER QUALITY OR LEAKS USING APPLIANCE DATA AND MACHINE LEARNING

TECHNICAL FIELD

The present disclosure relates to a system for sensing water quality and/or leaks via machine learning models that use data from appliances.

BACKGROUND

People use indoor plumbing every day. Examples of household items and fixtures that utilize indoor plumbing include hot-water tanks, showers, baths, toilets, washing machines, dishwashers, and even modern refrigerators. But indoor plumbing is often at risk for large disasters. People count on water quality in their homes, but rely on a private well or a single service provider to deliver the water (e.g., municipal utility company or the city's water and sewer commissions). People have high-pressure water for several uses, but this can create a disaster if an appliance or the plumbing leaks. Leaking water can damage almost anything it touches within a home.

Water-quality monitoring systems typically use expensive lab tests (e.g., performed by the municipal utility company) or a whole-home filtration system that is often unnecessary. The water supplier does not always succeed in detecting contamination.

Water leak detection systems are fairly primitive, but typically rely on a sensor that can detect a change in water flow properties within the plumbing.

SUMMARY

In an embodiment, a system for monitoring quality of water or leaks within a household plumbing system via a machine learning model is provided. The system includes a plurality of appliances connectable to a plumbing system to utilize water from the plumbing system, wherein each appliance includes one or more sensors configured to output sensor data regarding a property of the water being utilized by that appliance, and wherein each appliance has a transceiver configured to deliver the sensor data to a remote server. The system includes storage configured to maintain the sensor data. The system includes a processor in communication with the one or more sensors and the storage, the processor programmed to: receive a first set of the sensor data via the transceiver, establish boundaries of normal operation based on the first set of the sensor data, receive a second set of the sensor data, using a machine learning model, classify the second set of the sensor data into one or more labels indicating the property of the water being outside of the boundaries of normal operation, and based on the classifying of the second set of the sensor data indicating the property of the water being outside of the boundaries of normal operation, generate an output signal via the machine learning model in which the output signal indicates a presence of a water leak or degradation of water quality.

In an embodiment, a non-transitory computer readable medium is provided that includes instructions that, when executed by a processor, causes the processor to execute a set of functions, the set of functions comprising: receive a first set of sensor data from one or more sensors regarding a property of water being utilized by one or more appliances utilizing water from a plumbing system; establish boundaries of normal operation based on the first set of the sensor data; receive a second set of sensor data from the one or more sensors regarding the property of water being utilized by the one or more appliances; executing a machine learning model to classify the second set of the sensor data into one or more labels indicating the property of the water being outside of the boundaries of normal operation; and based on the classifying of the second set of the sensor data indicating the property of water being outside of the boundaries of normal operation, generating an output signal via the machine learning model in which the output signal indicates a presence of a water leak or degradation of water quality.

In an embodiment, a system for monitoring water quality or water leaks includes a plurality of appliances each having one or more sensors configured to output sensor data regarding a property of water being utilized by one or more of the appliances. The system includes storage configured to maintain the sensor data. The system includes a processor in communication with the one or more sensors and the storage, the processor programmed to: receive a first set of the sensor data from the one or more sensors, using a machine learning model, classify the first set of the sensor data into one or more labels indicating a property of the water being within established boundaries, updating the established boundaries utilizing the machine learning model based on the classified first set of sensor data, receive a second set of the sensor data from the one or more sensors, using the machine learning model, classify the second set of the sensor data into one or more labels indicating the property of the water being outside of the updated established boundaries, and based on the classifying of the second set of the sensor data indicating the property of the water being outside of the updated established boundaries, generate an output signal associated with a presence of a water leak or degradation of water quality.

DETAILED DESCRIPTION

Figure 1:
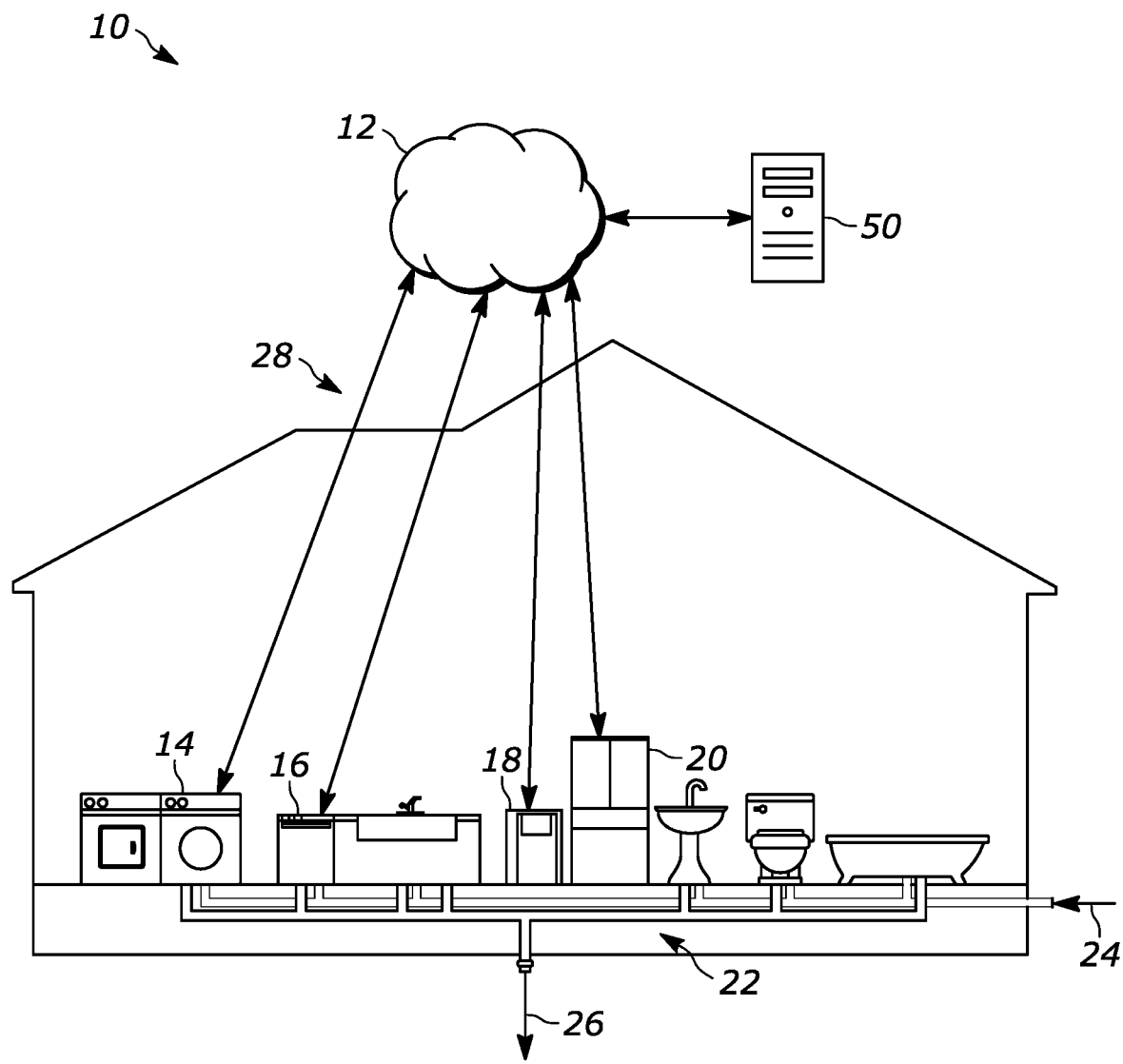
FIG. 1 is a schematic illustration of a system within a building with appliances that can communicate data to a remote server or off-site storage, such as the cloud, according to an embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The terminology used herein describes particular embodiments only and should not be construed to limit any embodiments disclosed herein. As used herein, the singular forms "a," "an," and "the" are intended to include the plural forms as well, unless the context clearly indicates otherwise.

Residential buildings (e.g., houses, condominiums, etc.), commercial buildings (e.g., stores, warehouses, etc.) and other buildings rely on indoor plumbing every day. Various appliances can be connected to the plumbing for utilization of water during operation. These appliances include, but are not limited to, hot-water heaters, boilers, washing machines, dishwashers, refrigerators, freezers, and others. But indoor plumbing is often at risk for large disasters. For example, a leak can be detrimental to not only the appliance and the plumbing itself, but to the structural integrity and appearance of the building. It is very often the case that a person does not know there is a leak until it's too late and severe damage to the building has already taken place.

Also, people count on the water quality distributed throughout the building. Water-quality monitoring systems typically use expensive lab tests (e.g., performed by the municipal utility company) or a whole-home filtration system that is often unnecessary. The water supplier does not always succeed in detecting contamination.

Therefore, according to various embodiments described herein, a system for detecting water quality and/or leaks in the indoor plumbing of a building is provided. This can be referred to as a whole-home (or whole-building) water quality system, for example. In embodiments, the system can rely on data sensed by the appliances themselves regarding the water being supplied to it. The type of data sensed by the appliances regarding the supplied water can include water pressure, water acidity (pH), water temperature, voltage, and others as will be described herein.

FIG. 1 is a schematic illustration of a system 10 for sensing water quality and/or events (e.g., leaks) via machine learning models, according to an embodiment. This illustration shows the system 10 configured for use within a house, but it should be understood that the systems described herein can be used in other residential buildings, and commercial buildings, and whatever other buildings may have one or more appliance that is connected to an indoor plumbing system. They can also apply to outdoor plumbing that is connected to appliances, such as irrigation systems or lawn sprinklers. The system may include one or more appliances with associated sensors and transceivers that can communicate data to off-site storage, such as the cloud 12, according to an embodiment. The appliances may include, for example, a washing machine 14 (e.g., a clothes washer), a dishwasher 16, a boiler 18, and a refrigerator 20. Other appliances in the system may include a hot water heater, a freezer, an ice machine, a steam oven, and any other type of home appliance connected to indoor plumbing. Other items that may be connected to the system 10 may include non-appliances, such as sinks, toilets, bath tubs, showers, an aquarium or fish tank, and the like that may also include the sensor and wireless communication capabilities disclosed herein. While references are made herein to "appliances" used in the system 10, it should be understood that the system is not limited to only including home appliance but can also include these non-appliance items or fixtures.

As shown in FIG. 1, an indoor plumbing system 22 delivers water from an external water source (e.g., a well, a municipal utility company's water source, etc.) to the house at 24, and can send dirty or used water out of the house at 26. Each of the appliances 14-20 is connected to the plumbing system 22 to receive water therefrom.

Each appliance may be referred to as an "internet of things" device, or IoT device. As such, each appliance can have an addressable interface (e.g., an Internet protocol (IP) address, a Bluetooth identifier (ID), a near-field communication (NFC) ID, etc.) and can transmit information to one or more other devices over a wired or wireless connection. Each appliance may have a passive communication interface, such as a quick response (QR) code, a radio-frequency identification (RFID) tag, an NFC tag, or the like, or an active communication interface, such as a modem, a transceiver, a transmitter-receiver, or the like. Each appliance can have a particular set of attributes (e.g., a device state or status, such as whether the appliance is using water, how much water it is using, the flow rate of the water to the device, the quantity of water in the device, the temperature of the water to the device, the pressure of the water delivered to the device, and the like as will be described further herein. Other set of attributes may include whether the appliance is on or off, open or closed, idle or active, available for task execution or busy, a cooling or heating function, an environmental monitoring or recording function, a light-emitting function, a sound-emitting function, etc.). These set of attributers can be embedded in and/or controlled/monitored by one or more central processing unit (CPU), microprocessor, ASIC, or the like, and configured for connection to a network 28 such as a local ad-hoc network or the Internet. The network 28 can be any wireless network configured to deliver data regarding the appliances to the cloud 12 or other offsite database and/or associated control system configured to apply the machine learning models described herein for sensing water quality delivered to the appliances and/or leaks within the plumbing system 22.

Figure 2:
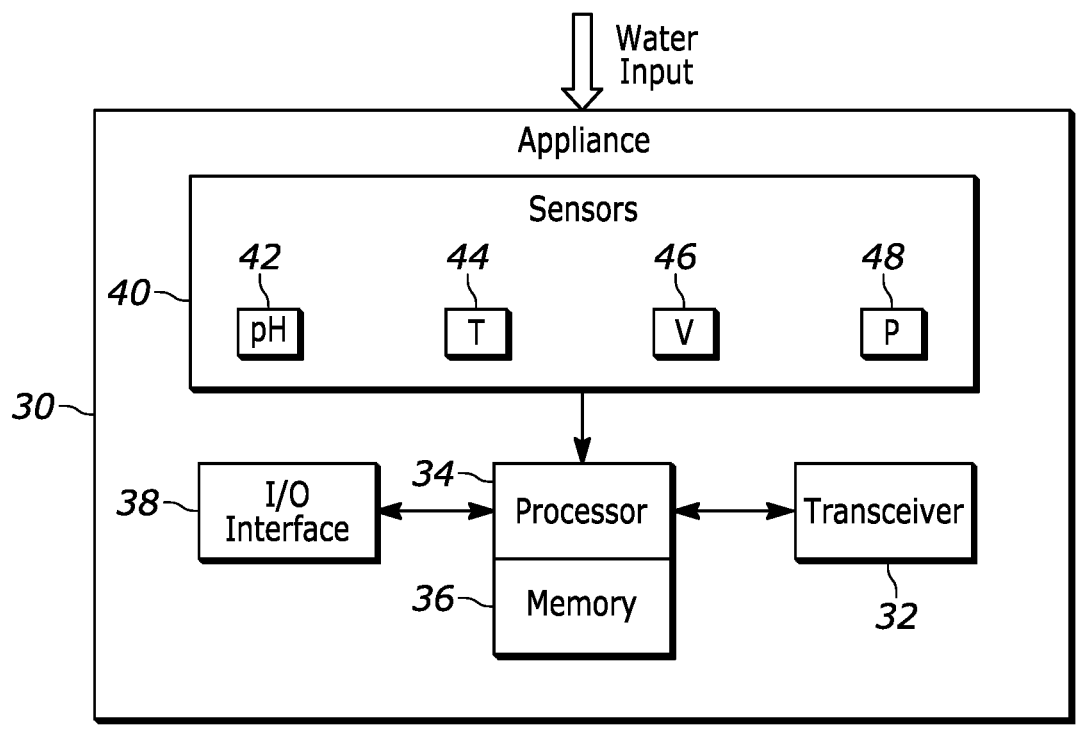
FIG. 2 is an example of various sensors in an appliance connected to the plumbing system, according to an embodiment.

While internal components of the appliances can be embodied with different hardware configurations, a high-level configuration for internal hardware components of one of the appliances is shown as platform 30 in FIG. 2 as an example. The platform 30 can receive and execute software applications, data and/or commands transmitted over a network interface. The platform 30 can also independently execute locally stored applications. The platform 30 can include one or more transceivers 32 configured for wired and/or wireless communication (e.g., a Wi-Fi transceiver, a Bluetooth transceiver, a cellular transceiver, a satellite transceiver, a GPS or SPS receiver, etc.) operably coupled to one or more processors 34, such as a microcontroller, microprocessor, application specific integrated circuit, digital signal processor (DSP), programmable logic circuit, or other data processing device, which will be generally referred to as processor 34. The transceiver 32 can include transceiver circuitry configured to transmit and/or receive information (e.g., data from the sensors disclosed herein) and can include a wireless communications interface (e.g., Bluetooth, Wi-Fi, Wi-Fi Direct, Long-Term Evolution (LTE) Direct, etc.) such as a wireless transceiver and associated hardware (e.g., an RF antenna, a MODEM, a modulator and/or demodulator, etc.). The processor 34 can execute application programming instructions within a memory 36 of the appliance. The memory 36 can include one or more of read-only memory (ROM), random-access memory (RAM), electrically erasable programmable ROM (EEPROM), dynamic random access memory (DRAM), static random access memory (SRAM), flash memory, or any memory common to computer platforms. An input/output (I/O) interface 38 can be configured to allow the processor 34 to communicate with and control various I/O devices such as a display, a power button, control buttons, and other devices such as sensors 40, actuators, relays, valves, switches, and the like associated with the appliance.

The sensors 40 may be located on the appliances and coupled to the water fed to the appliance via the plumbing system such that the sensors 40 can detect certain qualities about the water. For example, the sensors 40 may include an acidity sensor or pH sensor 42 configured to detect the acidity or pH of the water. This sensor 42 may be associated with water quality or contamination. For example, if a pH reading of the water is outside of a threshold (e.g., not within 6.5 and 8.5), this may be associated with contamination in the water.

The sensors 40 may include a temperature sensor 44 configured to detect a temperature of the water. This sensor 40 may be associated with issues with a heat exchanger within the house. For example, temperature readings deviating from the norm or outside of a threshold (e.g., not within 50 to 100 degrees C.) depending on the appliance may indicate there is an issue with the heat exchanger within the house, and the water is not being properly heated or cooled.

The sensors 40 may include a voltage sensor 46 configured to detect the electrochemical potential of the water versus a known electrode. These readings can be combined with pH measurements to help identify contaminants within the water.

The sensors 40 may include a pressure sensor 48 configured to detect the pressure of the water being delivered to the appliance. This sensor may be associated with water leaks. For example, a typical household water pressure in the United States is between 45-80 pounds per square inch (psi), depending on the appliance. Pressure measurements deviating from an established norm or given threshold for that particular house or particular make/model of appliance may indicate a potential leak in the plumbing system.

The sensors 40 may also include other sensors, such as a flow rate sensor, a dissolved oxygen (DO) sensor, and a turbidity sensor. The flow rate sensor may be configured to measure the flow rate of the water delivered to the appliance, and can be closely related to the pressure measurements. This determined data can serve as a proxy for the pressure measurements (or vice versa) if geometries are known. The dissolved oxygen sensor may be configured to determine dissolved oxygen concentrations in the water, and can be associated with water quality or contamination. The turbidity sensor may be configured to measure the amount of light that is scattered by suspended solids in the water, thereby determining the water clarity and/or if contaminants are in the water. For example, an exemplary appliance may be a fish tank or aquarium connected to the water system, and the dissolved oxygen, temperature, and turbidity sensors can be used to inform of the quality of the water within the tank.

Sensory data and signals determined from the sensors 40 may be routed internally to the transceiver 32, whereupon the transceiver 32 can deliver the data to an off-board server (e.g., the cloud 12) via the wireless network 28. The off-board server can then communication instructions or information back to the appliances, or to a mobile device 50. The mobile device can be a cellphone, tablet, computer, laptop, or the like to inform a user (e.g., homeowner or service technician) of a potential leak or water contamination. The mobile device 50 may be the homeowner's mobile device and configured to alert the homeowner of an issue in the plumbing system 22 for example. Alternatively, the mobile device 50 may be a service provider's mobile device and configured to alert the service provider of an issue in the plumbing system 22 so that the service provider can contact the homeowner, schedule a technician to arrive at the home to diagnose or fix the issue with the plumbing system 22. The notification may be, without limitation, through SMS, email, phone call, smartphone or smartwatch push notification, or lights or sounds directly on the appliance(s).

Figure 3:
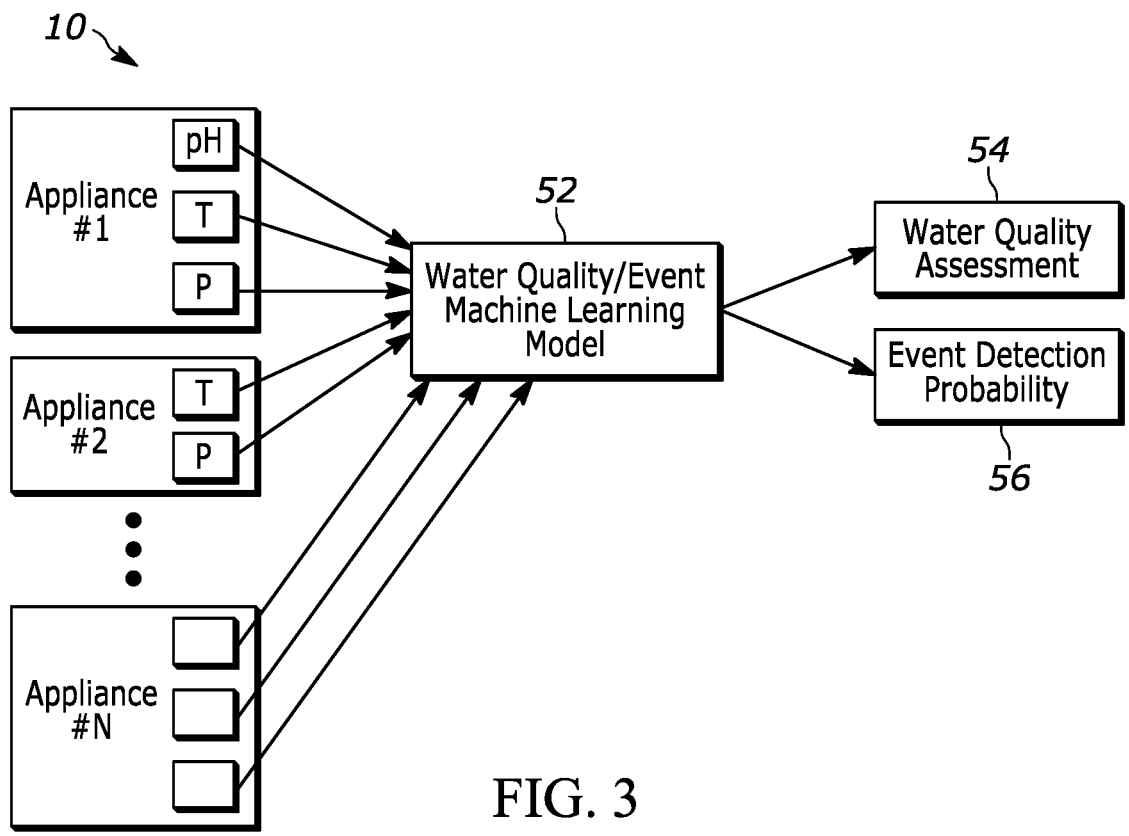
FIG. 3 is a flowchart of a system for detecting water quality or events (e.g., leaks) utilizing data from various appliances, according to an embodiment.

FIG. 3 illustrates a flowchart of the system 10 for detecting water quality or events (e.g., leaks) utilizing data from various appliances, such as those described above with reference to FIG. 1. Each appliance in the system 10 can communicate to the remote server in the cloud via the communication systems described above. The remote server can contain and maintain a water quality/event machine learning model 52 that will be described more fully below. The output of the water quality/event machine learning model 52 allows the system 10 to assess water quality at 54, and detect a probably of an event occurring at 56, such as a leak in the plumbing system 22 or other such disturbance to the water being delivered to the appliances.

As described above, each appliance can have any number of sensors described herein that are configured to detect information that can be processed on-board that appliance and/or sent to the remote server for processing. In the embodiment of FIG. 3, Appliance #1 includes a pH sensor 42, a temperature sensor 44, and a pressure sensor 48, and Appliance #2 includes a temperature sensor 44 and a pressure sensor 48. Other appliances in the same household (e.g., registered by the same user or within the same account) may be connected to the system 10, and each of the appliances may have any configuration or arrangement of sensors 40 described herein. This would allow for the system 10 to, for example, monitor water data across the household via the water quality/event machine learning model 52 to determine what data would constitute normal operation and what data would constitute an abnormality and a potential issue with the plumbing system 22. For example, as will be described below, the water quality/event machine learning model 52 can determine a drop in water pressure at a particular appliance, and the water quality/event machine learning model 52 can be trained to determine that this drop signifies a potential leak in the plumbing system 22 at a particular location upstream of the appliance showing the pressure drop. An associated upper threshold and lower threshold can be determined by the water quality/event machine learning model 52, and can define the boundaries of the normal operation, with any actual, prolonged, or trending sensory data falling outside those thresholds triggering an output that signifies a leak of potential quality issue with the water. As an example, the water quality/event machine learning model 52 can classify or differentiate between a pressure drop that is indicative of a leak, and a pressure drop that is indicative of something else (for example, someone running a bath or using water elsewhere in the household that would cause a slight pressure disturbance). These determinations may impact where the boundaries of normal operation reside, such that these instances of pressure drops do not signify a leak in the plumbing system.

Additionally, appliances from multiple different households or accounts may be part of the system 10. This allows the water quality/event machine learning model 52 to, for example, compare data between similar make (e.g., manufacturer or brand) and models of appliances from different households. In general, this would allow the water quality/event machine learning model 52 to understand what data would constitute normal operation, and what data would constitute an abnormality and a potential issue with the plumbing system associated with the particular appliance subject to the abnormality.

Figure 4:
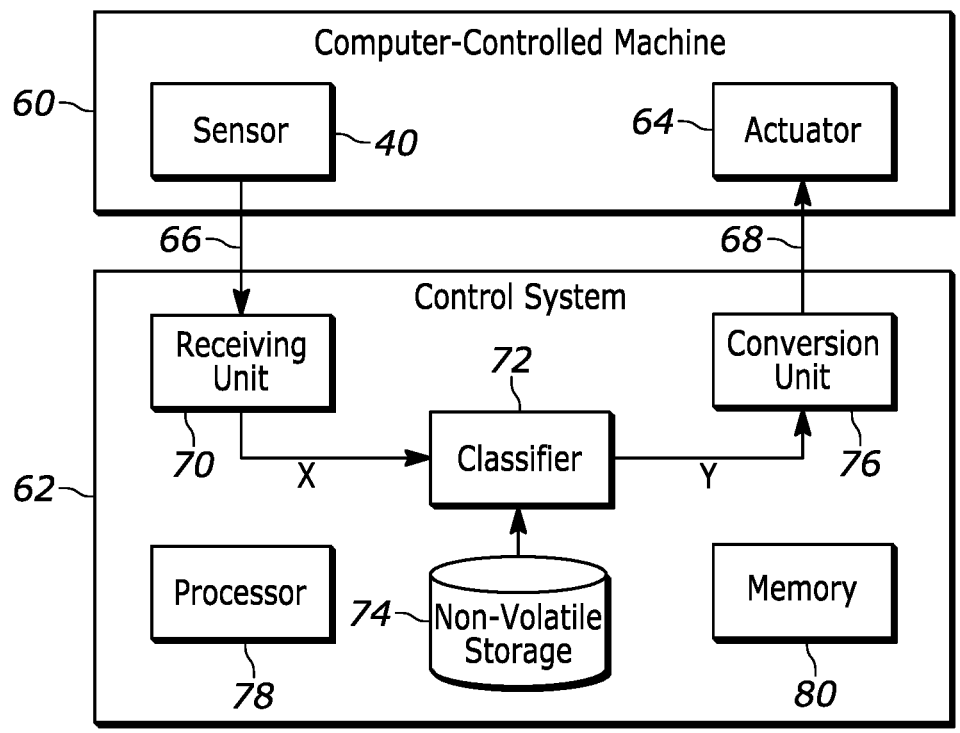
FIG. 4 is a schematic diagram of an interaction between a computer-controlled machine and a control system according to an embodiment.

FIG. 4 illustrates a schematic diagram of an interaction between a computer-controlled machine 60 and a control system 62 according to an embodiment. The computer-controlled machine 60 may be one or more of the appliances described herein. The computer-controlled machine 60 may also be a valve within the plumbing system 22 or within one of the appliances configured to control water flow within the plumbing system 22. The control system 62 may be a remote server. The control system 62 may be located at least partially within the cloud or remote server. The control system 62 may be located entirely at the remote server, wherein the computer-controlled machine 60 merely relays data for processing and execution at the remote server, and in turn, the remote server relays control signals to the computer-controlled machine 60 based on the processed data. It should be understood that FIG. 4 is merely a schematic illustration and is but one example of a possible layout of signal flow. This is not intended to be limiting on the scope of this disclosure unless expressly noted. The computer-controlled machine 60 and the control system 62 may all be located within the same household, within the same appliance, or may at least partially utilize or incorporate an off-site server such as the cloud; FIG. 4 is not intended to limit the system 10 to any one type of layout of data detection, computation, and control.

The computer-controlled machine 60 includes sensor 40 and actuator 64. The sensor 40 and actuator 64 may be within the same physical unit (e.g., an appliance), or may be in different physical units (e.g., the sensor 40 within the appliance and the actuator 64 being the mobile device 50 or a valve within the plumbing system 22). Sensor 40 may include one or more of the sensors described herein, and actuator 64 may include one or more actuator. Sensor 40 is configured to sense a condition of computer-controlled machine 60, such as the pressure, temperature, pH, and the like of the water fed into the computer-controlled machine 60. Sensor 40 may be configured to encode the sensed condition into sensor signals 66 and to transmit sensor signals 66 to control system 62 either directly or indirectly via the communication capabilities disclosed herein.

Control system 62 is configured to receive sensor signals 66 from computer-controlled machine 60. As set forth below, control system 62 may be further configured to compute actuator control commands 68 depending on the sensor signals 66 and to transmit actuator control commands 68 to actuator 64 of computer-controlled machine 60. In one general example, the control system 62 is configured to send an actuator control command 68 informing an actuator 64 (e.g., a water valve) to close based on signal processing indicating a potential leak in the plumbing system 22; the actuator 64 would in turn close based on the actuator control command 68. In another general example, the actuator 64 includes a system for sending notifications and/or scheduling an authorized technician or plumber to service the system to diagnose and fix the issue causing the alarm. In particular, the actuator 64 may include a scheduling event being created to the homeowner where the plumbing system 22 is located and/or a service technician for coming to the home. This will result in service technicians being notified of a problem (e.g., leak or contamination) in the plumbing system even before a homeowner even being aware of it.

As shown in FIG. 1, control system 62 includes receiving unit 70, or receiver. Receiving unit 70 may be configured to receive sensor signals 66 from sensor 40 (e.g., indirectly or directly from transceiver 32) and to transform sensor signals 66 into input signals x. In an alternative embodiment, sensor signals 66 are received directly as input signals x without receiving unit 70. Each input signal x may be a portion of each sensor signal 66. Receiving unit 70 may be configured to process each sensor signal 66 to produce each input signal x. Input signal x may include data corresponding to properties of the water (e.g., temperature, pressure, pH, etc.) as detected by sensor 40.

Control system 62 includes classifier 72. Classifier 72 may be configured to classify input signals x into one or more labels using a machine learning (ML) algorithm, such as a neural network. In one embodiment, the classifier 72 is configured to classify input signals x into one or more labels using the water quality/event machine learning model 52. Classifier 72 is configured to be parameterized by parameters θ. Parameters θ may be stored in and provided by non-volatile storage 74. Classifier 72 is configured to determine output signals y from input signals x. Each output signal y includes information that assigns one or more labels to each input signal x. Classifier 72 may transmit output signals y to conversion unit 76. Conversion unit 76 is configured to covert output signals y into actuator control commands 68. Control system 62 is configured to transmit actuator control commands 68 to actuator 64 (either directly or indirectly via, for example, the transceiver 32), which is configured to actuate computer-controlled machine 60 in response to actuator control commands 68. In another embodiment, actuator 64 is configured to actuate computer-controlled machine 60 based directly on output signals y. As an example, the classifier 72 may be configured to classify input signals x as either "normal" or "abnormal" based upon the learned models and classifiers disclosed herein; when input signals are classified as abnormal, the system may send an output signal y causing a notification or action to remedy the potential issue with the water, according to embodiments described herein.

Sensor signals 66 may be sent via the transceiver 32, and actuator control commands 68 may be received by the transceiver 32. Meanwhile, the control system 62 may have its own transceiver or receiver (such as including receiving unit 70) for sending and receiving sensor signals 66 and actuator control commands 68.

Upon receipt of actuator control commands 68 by actuator 64, actuator 64 is configured to execute an action corresponding to the related actuator control command 68. Actuator 64 may include a control logic configured to transform actuator control commands 68 into a second actuator control command, which is utilized to control actuator 64. In one or more embodiments, actuator control commands 68 may be utilized to control a display instead of or in addition to an actuator. In an embodiment, actuator control commands 68 cause a message to be displayed on mobile device 50 or a display on one or more of the appliances. In another embodiment, actuator control commands 68 cause a valve in the appliance or plumbing system to be opened or closed.

As shown in FIG. 1, control system 62 also includes processor 78 and memory 80. Processor 78 may include one or more processors. Memory 80 may include one or more memory devices. The classifier 72 (e.g., ML algorithms such as water quality/event machine learning model 52) of one or more embodiments may be implemented by control system 62, which includes non-volatile storage 74, processor 78 and memory 80.

Non-volatile storage 74 may include one or more persistent data storage devices such as a hard drive, optical drive, tape drive, non-volatile solid-state device, cloud storage or any other device capable of persistently storing information. Processor 78 may include one or more devices selected from high-performance computing (HPC) systems including high-performance cores, microprocessors, micro-controllers, digital signal processors, microcomputers, central processing units, application specific integrated circuit, field programmable gate arrays, programmable logic circuit, state machines, analog circuits, digital circuits, or any other devices that manipulate signals (analog or digital) based on computer-executable instructions residing in memory 80. Memory 80 may include a single memory device or a number of memory devices including, but not limited to, random access memory (RAM), volatile memory, non-volatile memory, static random access memory (SRAM), electrically erasable programmable ROM (EEPROM), dynamic random access memory (DRAM), flash memory, cache memory, or any other device capable of storing information.

Processor 78 may be configured to read into memory 80 and execute computer-executable instructions residing in non-volatile storage 74 and embodying one or more ML algorithms and/or methodologies of one or more embodiments described herein, such as the water quality/event machine learning model 52. Non-volatile storage 74 may include one or more operating systems and applications. Non-volatile storage 74 may store compiled and/or interpreted from computer programs created using a variety of programming languages and/or technologies, including, without limitation, and either alone or in combination, Java, C, C++, C#, Objective C, Fortran, Pascal, Java Script, Python, Perl, and PL/SQL. Non-volatile storage 74 and memory 80 may more generally be referred to as storage.

Upon execution by processor 78, the computer-executable instructions of non-volatile storage 74 may cause control system 62 to implement one or more of the ML algorithms and/or methodologies as disclosed herein. Non-volatile storage 74 may also include ML data (including data parameters) supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

The processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

In general, the classifier 72 and/or the water quality/event machine learning model 52 is trained to learn a function that provides a precise correlation between input values and output values. At runtime, a machine learning engine uses the knowledge encoded in the machine learning model 52 or classifier 72 against observed data to derive conclusions such as a diagnosis or a prediction. It is contemplated that the machine-learning algorithm may employ known machine-learning classification algorithms like linear classifiers, support vector machines, decision trees, boosted trees, random forest, neural networks, or nearest neighbor.

Figure 5:
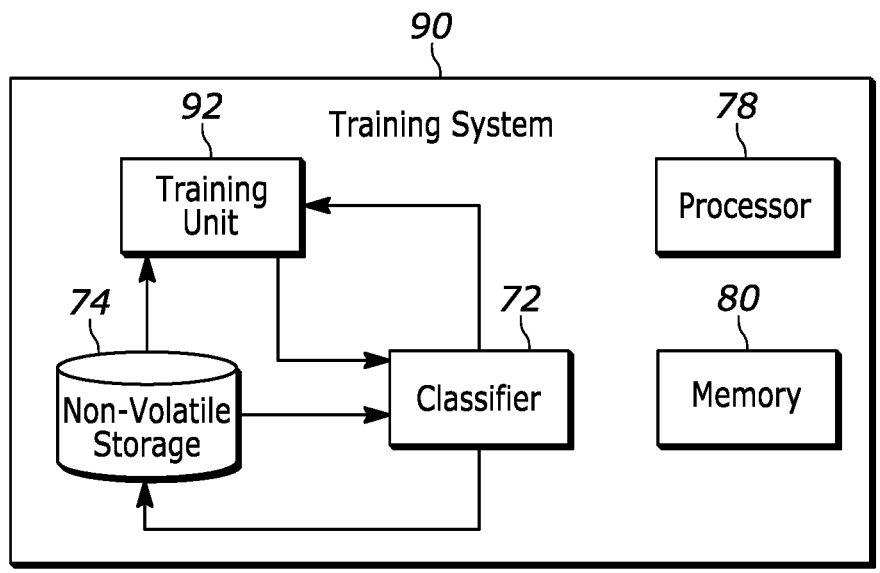
FIG. 5 is a schematic diagram of a training system for training a classifier according to an embodiment.

FIG. 5 illustrates a schematic diagram of a training system 90 for training the classifier 72 according to an embodiment. Training unit 92 is configured to determine input signals x and to transmit input signals x to classifier 72. In one embodiment, training unit 92 is configured to access non-volatile storage 74 to obtain a set of training data $X=\{(x1, y1), \ldots, (xn, yn)\}$ stored thereon. Non-volatile storage 74 also stores a loss function L. Non-volatile storage 74 may also store a set of class-dependent allowed perturbations. Furthermore, the training system 90 may include processor 78 and memory 80. The non-volatile storage 74, processor 78, and memory 80 may each be or include similar structure as those components described above with respect to FIG. 4. Alternatively, one or more of the non-volatile storage 74, processor 78, and memory 80 may be a different unit than that of FIG. 4, albeit with structure similar to the examples described above. The ML algorithms of one or more embodiments may be implemented by training system 90, which includes non-volatile storage 74, processor 78 and memory 80.

In general, training system 90 is configured to provide the ML algorithm(s) with training data to learn from. The training data contains sample input data and a correct answer (e.g., a target or target attribute). The ML algorithm(s) finds patterns in the training data that map the input data attributes to the target, and outputs an updated ML model that captures these patterns. In one embodiment, the water quality/event machine learning model 52 is trained by being provided with a plurality of data runs, with each data run having sample data from sensors 40 regarding the qualities of the water in the plumbing system 22, along with a corresponding output such as the plumbing system operating normally, the plumbing system having a leak, or the water in the plumbing system being contaminated. The more data runs are made available, the more the water quality/event machine learning model 52 can apply learning techniques to associate water qualities meaning "normal operation" and other water qualities meaning "abnormal." In the event of an abnormal determination, the actuator control commands 68 can be sent.

The data runs input in the system 90 may include data associated with each make/model of each appliance to which the corresponding sensor is associated with. Across a plurality of homes having a common make/model appliance, the water quality/event machine learning model 52 would thus be trained to recognize normal and abnormal behavior of the water being fed to that make/model of appliance.

Training system 90 is configured to execute a robust training procedure P to find a solution or approximate solution to learn classifier f parameterized by θ such that a robust loss is minimized with respect to θ. The robust training procedure P may be an asymmetrical robust classifier configured to be trained by training system 90 by expanding a robust loss function to be class separable. This training results in K different robust loss functions computed over a partition of the training sets across K different classes. The final classifier parameters may be obtained by solving for the sum of the K different loss functions across the partition of the training sets.

Given the structure of the systems described in FIGS. 1-5, application and use of these systems for determining water quality or other events (e.g., a leak in the plumbing) will now be described. The system is able to detect an event, such as water leaks, or water contamination. Water leaks can include leaks in the pipes, leaks in the appliances, or leaks in other appliances that are not connected to the system 10 but are connected to the plumbing system 22. The system is also able to detect appliance lifetime and defects, such as fouled heat exchangers (whether through biofilm buildup or inorganic limescale buildup). The system is also able to detect water quality, such as pH value (acidity), which is associated with contaminants. For example, a sudden lowering of the pH value may cause corrosion of high-lead components of the plumbing system 22 through the following reaction:

$$Pb + 2H^+ + \frac{1}{2}O_2 \rightarrow Pb^{2+} + H_2O$$

Or, if the pH value is consistently high, special care would have to be taken to remove or prevent limescale buildup due to the following reaction:

$$Ca^{2+} + CO_3^{2-} \rightarrow CaCO_3$$

The machine learning models and classifiers disclosed herein can be configured to determine "an event" using a neural network, random forest, or other artificial-intelligence network disclosed herein. The network is trained on "normal" measurements and learns the type of events associated with a particular profile of sensor measurements. For example, the system can learn certain pressure drops that indicate normal usage of the plumbing system (such as someone turning on a faucet or drawing a bath). The measurements of the systems worldwide can be anonymized and fed into the network for training data. For example, the network can learn that a leak in the plumbing system 22 corresponds with an abnormal pressure reading from pressure sensor 48 being outside of a "normal" threshold or range. As another example, the network can learn that when a particular model of boiler starts registering lower-than-expected temperatures, it means there is biofilm buildup that needs to be removed, or that only a certain amount of time (e.g., six months) remains on the boiler's lifetime. As another example, the pH of a certain house can be learned as that plumbing system's "normal" pH, and a new reading deviating by the normal pH by a certain threshold can trigger the "event" as being a potential contamination.

Upon installation of one or more appliances configured to operate in the disclosed systems, the machine learning models are initialized to learn the "normal" measurements. To do so, the system may run the appliances to learn typical behavior of water flow, temperature, pressure, pH, and the other water qualities disclosed herein. This may establish a baseline upon which future data is measured against. This baseline may be established for each season (e.g., once in the summer and once in the winter) to establish baselines that account for changes in ambient environment which can effect these signal readings.

Additionally, when a new appliance is added to the system (e.g., a new model dishwasher, new water pressure valve, etc.) the user can activate a "learning mode" to establish a new baseline of measurements with the water properties. The user can also program the type of appliance and model into the system to give reasonable bounds of the measurements (e.g., a boiler will use much more water than a refrigerator), help interpret the results (e.g., a refrigerator that is using water at a rate above a threshold such as one gallon per minute likely has a leak, or a toilet having a constant draw of water likely has a leak), and feed anonymized data to the cloud.

In an embodiment, the systems disclosed herein can be combined with a smart-home control system. In the event of a possible leak detected, the system may control the water valves going to the at-risk appliances to reduce water pressure or shut them off temporarily until a maintenance check can be performed. It may optionally communicate directly with a service provider (e.g., property manager) to schedule the maintenance check. By way of example, data received by the classifier may cause the classifier to indicate a leak is probable in the house; the control system can then send a signal to a corresponding actuator to close a valve that would stop or reduce water flow to the area where the leak is determined to be.

Figure 6:
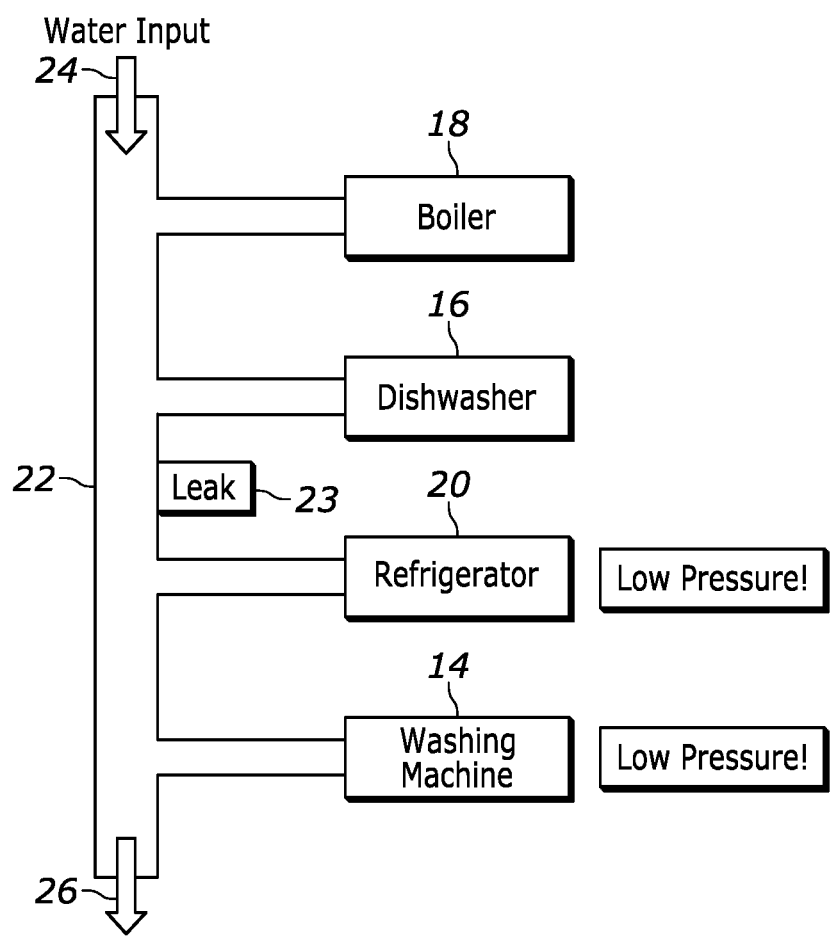
FIG. 6 illustrates a schematic diagram of a water flow into various appliances within a home or building, with a leak detected based on data from the appliances, according to an embodiment.

The systems disclosed herein also enable the location of the detected event (e.g., a leak) to be determined. Referring to FIG. 6, a plurality of appliances (e.g., washing machine 14 or laundry washer, dishwasher 16, boiler 18, and refrigerator 20) are connected to the plumbing system 22. The appliances are arranged such that the boiler 18 is located closest to the water input at 24. In other words, the boiler 18 is the most upstream appliance relative to the plumbing system 22. The next downstream appliance is the dishwasher 16, then the refrigerator 20, and finally the washing machine 14. The user can configure the system (e.g., through the I/O interface or mobile device) with the knowledge of the relative upstream locations of these appliances. Alternatively, the system is configured to automatically detect where each appliance is relative to the plumbing system 22 based on analysis of pressure and temperature realized at each appliance during use of one or more of the appliances.

With the knowledge of where each appliance is located along the plumbing system 22, the systems disclosed herein can determine a location of an event, in this case a leak 23. In particular, if a leak 23 occurs downstream of the dishwasher 16 but upstream of the refrigerator 20, then the refrigerator 20 and downstream appliances such as the washing machine 14 will experience water pressure abnormalities (e.g., low pressure). The pressure sensor 48 at each of the refrigerator 20 and washing machine 14 will detect a water pressure being lower than the established baseline or normal water pressure previously established via machine learning. Meanwhile, the pressure sensors 48 at each of the boiler 18 and dishwasher 16 may not experience such a pressure drop. Between the last downstream appliance that registers a normal water pressure (e.g., dishwasher 16 in this example) and the most upstream appliance that registers an abnormal water pressure (e.g., refrigerator 20) is the location where the system determines is the source of the leak.

Various notifications, recommendations, or automatic mitigation measures may be taken in response to the water quality/event machine learning model 52 detecting either a water quality issue at 54 or a probability of an abnormal event at 56. The notifications, recommendations, or automatic mitigation measures can be made via the actuator control commands 68 to, for example, turn on/off an appliance, open/close a valve in the plumbing system to mitigate the leak, or schedule notify a user via mobile device 50, schedule a technician for service, or other such measures described herein.

If a determined event is a water leak in the plumbing system 22 based on the water pressure being lower than its normal bounds, a notification can be sent to a user (e.g., homeowner, service provider) to check fixtures for collected water. Such a notification can be present on the user's mobile device 50. Also, an alert may be made on the mobile device that the municipality (e.g., the water company) should be contacted. In addition, the alert may inform the homeowner to call a plumber, and may access the mobile device's list of contacts for a plumber, and suggest the user contact that plumber.

If a determined event is a contamination based on the pH of the water being outside of the normal bounds, a notification can be sent to the user with a message informing the user to use water sensor strips to test the pH of the water. For example, the water quality/event machine learning model 52 can establish a baseline of pH for the water in the user's plumbing system. If the change in pH over time changes, then corrosion of the piping within the plumbing system may be detected. The sending of the notification can be made well before a user may discover any problem with the water quality. The notification can also be present on the user's mobile device 50. The notification may additionally or alternatively inform the user to contact the municipality should be contacted. The notification can also inform the user to add a water purifier (e.g., reverse osmosis, filters, etc.) or used boiled or bottled water instead of the tap water.

If a determined event is with respect to the remaining lifetime of the appliance, a notification can be sent to the user with a message informing the user to inspect for limescale or biofilm (for example, in the boiler) as these may degrade the lifetime of the appliance. The notification can also be present on the user's mobile device 50. The notification may additionally or alternatively inform the user to contact an appliance technician, or the notification can automatically be routed directly to a service provider or technician whereupon they can contact the homeowner for an inspection.

Figure 7:
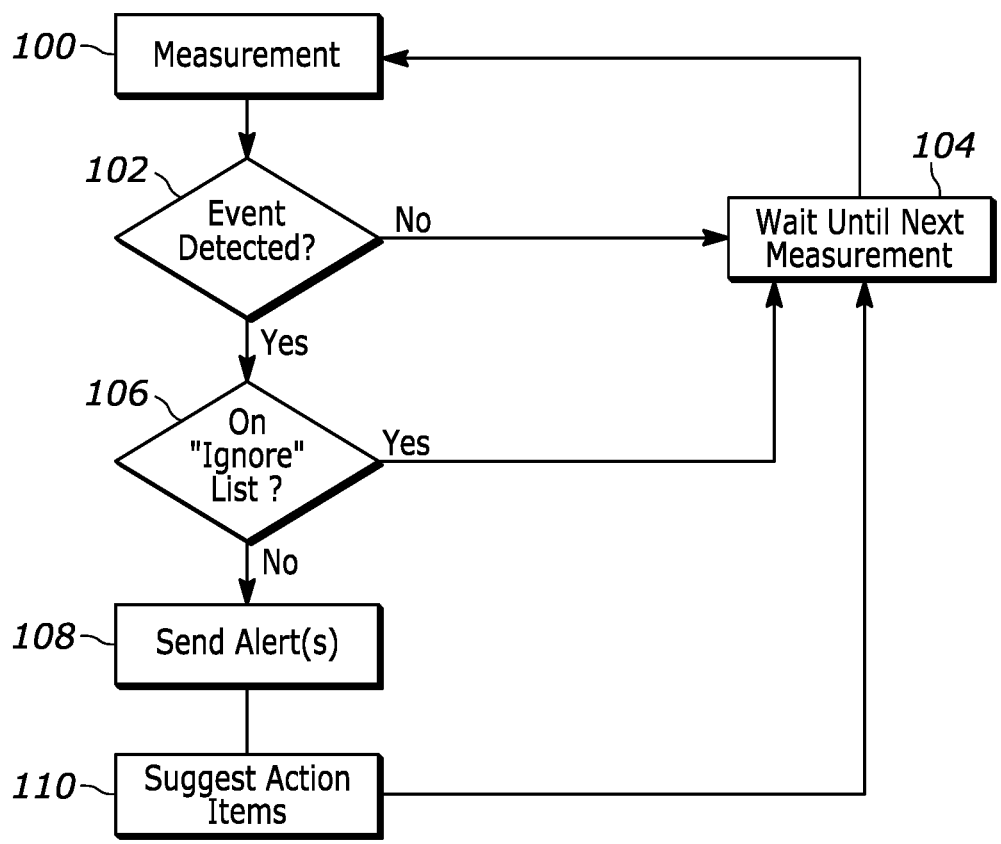
FIG. 7 illustrates a flow chart of a computational method for alerting a user of a water quality issue or leak based on the data from the appliances, according to an embodiment.

FIG. 7 illustrates a flowchart of an algorithm that can be implemented by the one or more processors described herein. At 100, a measurement is taken by one or more of the sensors 40. As described herein, the measurements from the sensors 40 can be transmitted via network 28 to an off-site server or the cloud 12. Data can be organized or filtered such that it can be retrieved per make/model of appliance, for example. This allows the system to establish a "normal operation" measurement via the training of the water quality/event machine learning model 52. Likewise, this allows the water quality/event machine learning model 52 to recognize whether a signal from one or more of the sensors 40 is outside the established norm, which may trigger whether an "event" is detected at 102. The event may be indicated by a drop in pressure below a threshold associated with "normal" after operating the water quality/event machine learning model 52. Or, the event may be indicated by an increase or decrease in temperature outside the established normal, or other such measurements and thresholds as described herein.

If there is no event detected—e.g., if the readings from the sensors 40 output data that is within the established normal operation measurements as determined by the water quality/event machine learning model 52—then the system merely waits until a next measurement at 104. The system returns to 100 for another measurement.

If there is an event detected, then at 106 the system first checks whether the detected event is on an "ignore" list. This "ignore" list can be user-customizable. For example, if the user previously received a notification that the water boiler has an estimated six months' lifetime, the user may order a replacement and place boiler-lifetime notifications on the "ignore" list for a customizable amount of time (e.g. two months). The "ignore" list can also be customized by the service provider. For example, if the municipal water provider alerted all users to a water contamination issue, it would be superfluous for each appliance to additionally alert the user to a water contamination issue on a daily basis. If the detected event is on the ignore list, the system proceeds to 104 and waits for a new measurement at 100.

If the detected event is not on an ignore list, the system proceeds to 108 in which an alert is sent. The alert may be sent to the user's mobile device 50, for example. The alert may be sent to a service provider's mobile device or personal electronic work space (e.g., email, etc.) The alert may also be sent to a technician, informing the technician of a potential event in need of servicing or at least inspecting.

The alert may include a suggested action item at 110. The suggested action item depends on the detected event. For example, as described above, if the determined event is a contamination based on the pH of the water being outside of the normal bounds, the notification can be sent to the user with a suggestion that the user use water sensor strips to test the pH of the water or use bottled water.

Other examples of using sensor data for use in the water quality/event machine learning model 52 is contemplated, and this disclosure is not intended to be limited to only the disclosed embodiments. By way of example, in other embodiments, the water quality/event machine learning model 52 can establish a baseline or "normal" operating temperature of the water that is used by the appliance (e.g., the hot water used by the washing machine 14). If the water temperature provided to the washing machine 14 no longer reaches this normal operating temperature, the system can alert the user that there may be a problem with the hot water heater or a heat exchanger. This will allow the user to fix the hot water heater before it completely fails, which is typically only realized once water is found on the ground beneath the hot water heater tank.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A system for monitoring quality of water or leaks within a household plumbing system via a machine learning model, the system comprising:
    a plurality of appliances of identical make and model, each appliance connectable to a respective one of a plurality of different plumbing systems to utilize water from the respective one of the plumbing systems, wherein each appliance includes one or more sensors configured to output sensor data regarding a property of the water being utilized by that appliance, wherein each appliance has a transceiver configured to deliver the sensor data to a remote server;
    a storage configured to maintain the sensor data; and
    a processor in communication with the one or more sensors and the storage, the processor programmed to:
        receive a first set of the sensor data via the transceiver,
        establish boundaries of normal operation based on the first set of the sensor data,
        receive a second set of the sensor data,
        using a machine learning model, classify the second set of the sensor data into one or more labels indicating the property of the water being outside of the boundaries of normal operation, and
        based on the classifying of the second set of the sensor data indicating the property of the water being outside of the boundaries of normal operation, generate an output signal via the machine learning model in which the output signal indicates a presence of a water leak or degradation of water quality.

2. The system of claim 1, wherein the one or more labels includes a label of normal operation and a label of abnormal operation.

3. The system of claim 1, wherein the one or more sensors includes a pressure sensor and the property of the water is water pressure.

4. The system of claim 3, wherein the output signal indicates a presence of a water leak in response to the classifying of the second set of the sensor data indicating the water pressure being outside of the boundaries of normal operation.

5. The system of claim 1, wherein the one or more sensors includes a pH sensor and the property of the water is acidity.

6. The system of claim 5, wherein the output signal indicates a degradation of water quality in response to the classifying of the second set of the sensor data indicating the acidity being outside of the boundaries of normal operation.

7. The system of claim 1, wherein the output signal is configured to turn off one of the appliances associated with the second set of the sensor data or close a valve associated with the second set of the sensor data.

8. A non-transitory computer readable medium including instructions that, when executed by a processor, causes the processor to execute a set of functions, the set of functions comprising:
    receive a first set of sensor data from one or more sensors regarding a property of water being utilized by a plurality of appliances utilizing water from a respective plurality of household plumbing systems, wherein the appliances are of identical make and model;
    establish boundaries of normal operation based on the first set of the sensor data;
    receive a second set of sensor data from the one or more sensors regarding the property of water being utilized by the one or more appliances;
    executing a machine learning model to classify the second set of the sensor data into one or more labels indicating the property of the water being outside of the boundaries of normal operation; and
    based on the classifying of the second set of the sensor data indicating the property of water being outside of the boundaries of normal operation, generating an output signal via the machine learning model in which the output signal indicates a presence of a water leak or degradation of water quality.

9. The non-transitory computer readable medium of claim 8, wherein the one or more labels includes a label of normal operation and a label of abnormal operation.

10. The non-transitory computer readable medium of claim 8, wherein the one or more sensors includes a pressure sensor and the property of the water is water pressure.

11. The non-transitory computer readable medium of claim 10, wherein the output signal indicates a presence of a water leak in response to the classifying of the second set of the sensor data indicating the water pressure being outside of the boundaries of normal operation.

12. The non-transitory computer readable medium of claim 8, wherein the one or more sensors includes a pH sensor and the property of the water is acidity.

13. The non-transitory computer readable medium of claim 12, wherein the output signal indicates a degradation of water quality in response to the classifying of the second set of the sensor data indicating the acidity being outside of the boundaries of normal operation.

14. The non-transitory computer readable medium of claim 8, wherein the output signal is configured to turn off one of the appliances associated with the second set of the sensor data or close a valve associated with the second set of the sensor data.

15. A system for monitoring water quality or water leaks, the system comprising:
    a storage configured to maintain sensor data regarding a property of water being utilized by a plurality of appliances of identical make and model, each appliance connected to a respective one or a plurality of different plumbing systems; and a processor in communication with the storage and the plurality of appliances with each appliance having one or more sensors configured to output the sensor data, the processor programmed to:

receive a first set of the sensor data from the one or more sensors, using a machine learning model, classify the first set of the sensor data into one or more labels indicating a property of the water being within established boundaries, update the established boundaries utilizing the machine learning model based on the classified first set of sensor data, receive a second set of the sensor data from the one or more sensors, using the machine learning model, classify the second set of the sensor data into one or more labels indicating the property of the water being outside of the updated established boundaries, and based on the classifying of the second set of the sensor data indicating the property of the water being outside of the updated established boundaries, generate an output signal associated with a presence of a water leak or degradation of water quality.

16. The system of claim 15, wherein the processor is further programmed to:

receive a third set of the sensor data, using the machine learning model, classify the third set of the sensor data into one or more labels indicating the property of the water being outside of the updated established boundaries, determine the third set of the sensor data is associated with appliances that do not have the same make and model as the appliances associated with the first set of sensor data, and ignoring the third set of the sensor data by not generating the output signal based on the third set of the sensor data being associated with appliances that do not have the same make and model as the appliances associated with the first set of sensor data.

* * * * *